(12) United States Patent
Ren et al.

(10) Patent No.: US 12,735,338 B2
(45) Date of Patent: Sep. 15, 2026

(54) NANOCOMPOSITE PREPARATION, METHOD FOR MAKING THE SAME AND USE THEREOF

(71) Applicant: INSTITUTE OF SOIL SCIENCE, CHINESE ACADEMY OF SCIENCES, Nanjing (CN)

(72) Inventors: Wenjie Ren, Nanjing (CN); Ying Teng, Nanjing (CN); Yongming Luo, Nanjing (CN); Haoran Liu, Nanjing (CN); Rui Zhao, Nanjing (CN)

(73) Assignee: INSTITUTE OF SOIL SCIENCE, CHINESE ACADEMY OF SCIENCES, Nanjing (CN)

( * ) Notice: Subject to any disclaimer, the term of this patent is extended or adjusted under 35 U.S.C. 154(b) by 531 days.

(21) Appl. No.: 18/309,365

(22) Filed: Apr. 28, 2023

(65) Prior Publication Data

US 2024/0279099 A1 Aug. 22, 2024

(30) Foreign Application Priority Data

Feb. 22, 2023 (CN) ......................... 202310153778.5

(51) Int. Cl.
*C02F 3/34* (2023.01)
*B09C 1/10* (2006.01)
(Continued)

(52) U.S. Cl.
CPC ................ *C02F 3/348* (2013.01); *B09C 1/10* (2013.01); *C09K 17/42* (2013.01); *C12N 1/205* (2021.05);
(Continued)

(58) Field of Classification Search
CPC ... B09C 1/10; C12N 1/205; C02F 3/34; C02F 3/348; C09K 17/42
(Continued)

(56) References Cited

U.S. PATENT DOCUMENTS 7,915,027 B2 * 3/2011 Brigmon .................. B09C 1/10 435/262.5
2019/0071337 A1 * 3/2019 Razavi-Shirazi ....... C12P 39/00

FOREIGN PATENT DOCUMENTS

CN 107413841 B * 5/2020 ............ B09C 1/105
CN 111849956 A * 10/2020 ............ C09K 17/14

OTHER PUBLICATIONS

Liu et al, English Machine Translation CN 107413841, pp. 1-8 (Year: 2020).*

(Continued)

*Primary Examiner* — Claire A Norris
(74) *Attorney, Agent, or Firm* — Leason Ellis LLP

(57) ABSTRACT

The present invention relates to the field of environmental pollution remediation technology, in particular to a nanocomposite preparation and a method for making the same and use thereof. The nanocomposite preparation provided herein includes a nanomaterial and an extracellular polymeric substance (EPS) solution of a microorganism, where the nanomaterial is graphene oxide (GO) or multi-walled carbon nanotubes (CNT); and the microorganism is *Paracoccus aminovorans* HPD-2, deposited in China General Microbiological Culture Collection (CGMCC) Center, with a deposition number of CGMCC No. 2568. The nanomaterial and EPS system in the present disclosure may improve the bioeffectiveness of Polycyclic Aromatic Hydrocarbons (PAHs) in soil and thus the degradation of PAHs compared to a single system. The synergistic effect between the nanomaterial and the EPS of the degrading bacteria significantly improves the removal of PAHs from soil and water, thus greatly reducing the remediation cycle of the PAH-contaminated soil and water.

11 Claims, 4 Drawing Sheets

(51) Int. Cl.
*C02F 101/32* (2006.01)
*C09K 17/42* (2006.01)
*C12N 1/205* (2026.01)
*C12R 1/01* (2006.01)

(52) U.S. Cl.
CPC .... *B09C 2101/00* (2013.01); *C02F 2101/327* (2013.01); *C12R 2001/01* (2021.05)

(58) Field of Classification Search
USPC .......................................................... 210/601
See application file for complete search history.

(56) References Cited

OTHER PUBLICATIONS

Ren et al. English machine translation CN 111849956, pp. 1-6 (Year: 2020).*

* cited by examiner

NANOCOMPOSITE PREPARATION, METHOD FOR MAKING THE SAME AND USE THEREOF

CROSS REFERENCE TO RELATED APPLICATION

This patent application claims the benefit and priority of Chinese Patent Application No. 2023101537785, entitled "NANOCOMPOSITE PREPARATION, METHOD FOR MAKING THE SAME AND USE THEREOF" filed on Feb. 22, 2023, the disclosure of which is incorporated by reference herein in its entirety as part of the present application.

TECHNICAL FIELD

The present disclosure belongs to the field of environmental pollution remediation technology, and specifically relates to a nanocomposite preparation, a method for making the same and use thereof.

BACKGROUND ART

Polycyclic Aromatic Hydrocarbons (PAHs) are a group of persistent organic pollutants consisting of two or more benzene rings fused together in a linear, angular or clustered form. PAHs mainly come from the incomplete combustion of fossil fuels and biomass, as well as from leaks and emissions during oil extraction, transportation, production and use. Due to their stable physicochemical properties, hydrophobicity and the "tri-causal" effect, PAHs are difficult to degrade when they contaminate soil and water bodies, and are becoming a global environmental concern.

At present, the main methods for removing PAHs include adsorption, chemical oxidation and biodegradation. For example, Chinese patent CN109748350A discloses an adsorbent for heavy metal and PAH contaminated water bodies and a remediation method; Chinese patent CN109650522A discloses a method of removing PAHs from water bodies using iron-manganese bimetallic oxide modified biochar photo-Fenton composites. Despite the high removal efficiency of adsorption and chemical oxidation methods, there are still problems of incomplete removal, high dosage of chemical materials leading to secondary pollution, and relatively high remediation costs.

Microbial remediation has the advantages of simple operation, low cost and no secondary pollution, etc. Some PAHs degrading microorganisms have been screened, for example, Chinese patent CN101348773A reports a strain *Paracoccus aminovorans* (*P. aminovorans*) HPD-2 that can degrade high molecular weight PAHs (benzo[a]pyrene, pyrene or fluoranthene), which has a broad substrate spectrum and has a good ability to degrade PAHs in the environment. However, in actual remediation projects, the exogenous microorganisms often have difficulty in functioning stably in the in situ soil and water environment due to the competition from indigenous microorganisms and environmental conditions, so that ideal remediation results cannot be achieved. Moreover, microbial remediation usually has problems such as low remediation efficiency and long remediation period.

SUMMARY

In view of the above, it is an objective of the present disclosure to provide a nanocomposite preparation and a method for making the same and use thereof. The nanocomposite preparation provided by the present disclosure may effectively degrade PAHs in contaminated soil and water bodies and shorten the remediation cycle.

In order to achieve the above objective, the present disclosure provides the following technical solutions.

The present disclosure provides a nanocomposite preparation including a nanomaterial and an extracellular polymeric substance (EPS) solution of a microorganism, where the nanomaterial is graphene oxide (GO) or multi-walled carbon nanotubes (CNT); the microorganism is *P. aminovorans* HPD-2, deposited in China General Microbiological Culture Collection (CGMCC) Center, with a deposition number of CGMCC No. 2568.

In some embodiments, an EPS in the EPS solution has a concentration of 2 to 16 gram/liter (g/L).

In some embodiments, a ratio between a mass of the nanomaterial and a volume of the EPS solution of the microorganism is 2-20 g:1 L.

The present disclosure further provides a method for preparing the nanocomposite preparation in the above technical solution, including the steps of:

- inoculating *P. aminovorans* HPD-2 in a culture medium and isolating a resulting culture system to obtain bacteria;
- washing and resuspending the bacteria to obtain a microbial solution;
- subjecting the microbial solution to sonication, centrifugation and filtration in turn to obtain the EPS solution of the microorganism; and
- dispersing the nanomaterial in the EPS solution of the microorganism to obtain the nanocomposite preparation.

In some embodiments, the microbial solution has an OD600 value of 0.6 to 1.2.

In some embodiments, the filtration is carried out using a 0.22 micrometer (μm) filter membrane.

In some embodiments, the sonication is conducted at room temperature for 10 min with a power of 240 W.

The present disclosure further provides use of the nanocomposite preparation described in the above technical solution, or a nanocomposite preparation prepared by the method described in the above technical solution in the remediation of PAH-contaminated water and/or PAH-contaminated soil.

In some embodiments, a volume of the nanocomposite preparation is 2.5% of a volume of the PAH-contaminated water.

In some embodiments, the nanocomposite preparation is 10% by dry weight of the PAH-contaminated soil.

The present disclosure provides a nanocomposite preparation including a nanomaterial and an EPS solution of a microorganism, where the nanomaterial is GO or multi-walled CNT; and the microorganism is *P. aminovorans* HPD-2, deposited in CGMCC Center, with a deposition number of CGMCC No. 2568.

The nanomaterial in the nanocomposite preparation provided by the present disclosure may, on the one hand, provide a carrier for the EPS and PAHs to come into contact with each other and enrich both PAHs and the EPS, thus accelerating the interaction between the EPS and PAHs, and on the other hand, accelerate the electron transfer process during the degradation of PAHs by the EPS. In addition, the nanomaterial and EPS system may improve the bioeffectiveness of PAHs in soil, compared with a single system, thus accelerating and improving the degradation of PAHs. The present disclosure makes full use of the high surface activity of the nanomaterial and the degradation properties of the EPS of the degrading bacteria, and the synergistic effect between the two significantly accelerates and enhances the degradation and removal of PAHs from soil and water, increasing the degradation and removal rate of PAHs, thus greatly shortening the remediation cycle of PAH-contaminated soil and water.

In addition, the nanocomposite preparation is simple, cost-effective, and has the prospect of large-scale industrial production. It is suitable for the in-situ remediation of PAH-contaminated soil and water without secondary contamination.

DETAILED DESCRIPTION OF THE EMBODIMENTS

Figure 1:
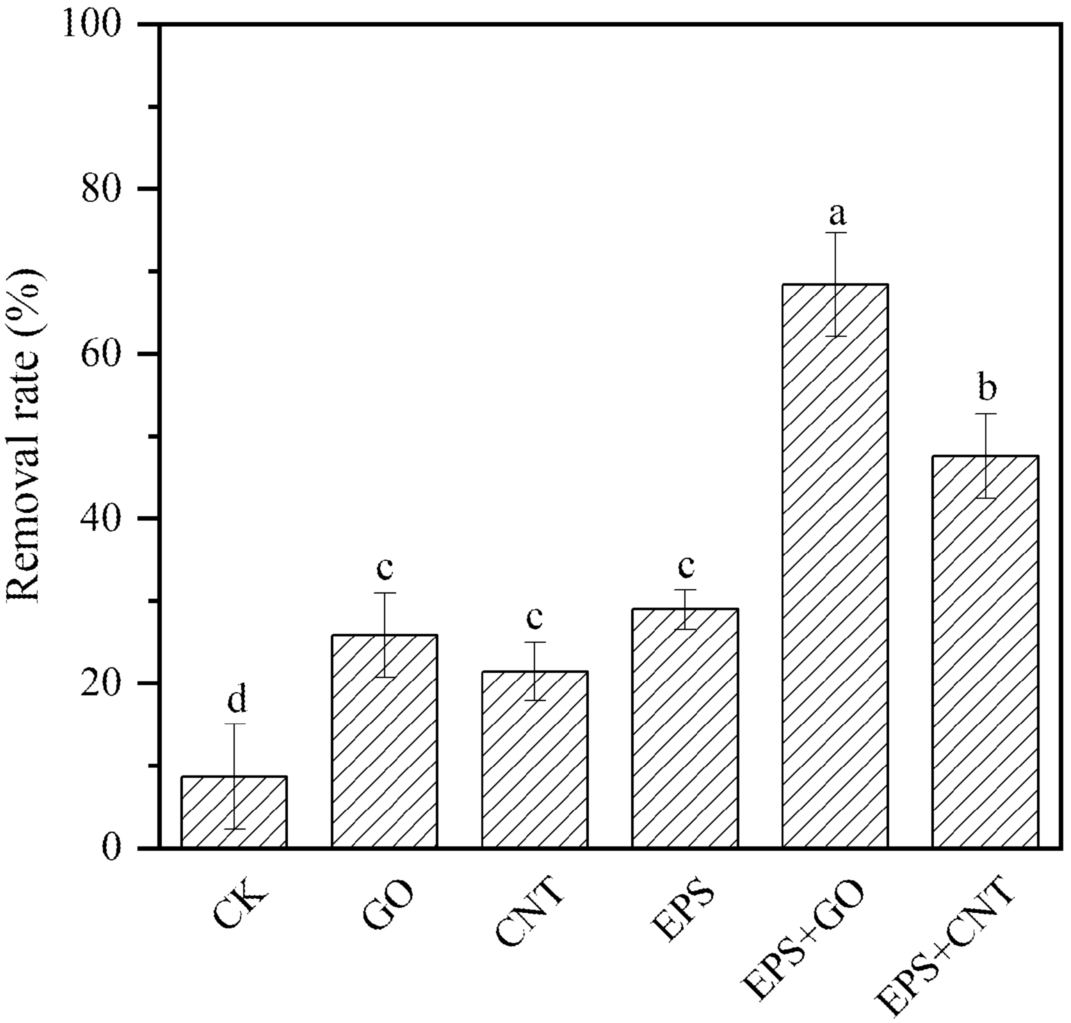
FIG. 1 shows a histogram of the removal rate of benzo [a]pyrene (BaP) from the soil after incubation in Application Examples 1 to 2 and Comparative Application Examples 1 to 4 of the present disclosure.

The present disclosure provides a nanocomposite preparation including a nanomaterial and an EPS solution of a microorganism, where the nanomaterial is GO or multi-walled CNT; the microorganism is *P. aminovorans* HPD-2, deposited in CGMCC Center, with a deposition number of CGMCC No. 2568.

If not otherwise specified, in the present disclosure, there is no special requirement on the source of raw materials used, and commercially available commodities known to those skilled in the art can be used.

The nanocomposite preparation provided by the present disclosure includes a nanomaterial; and the nanomaterial is GO or multi-walled CNT, preferably GO.

The nanocomposite preparation provided by the present disclosure includes an EPS solution of a microorganism; the microorganism is *P. aminovorans* HPD-2, deposited in CGMCC Center, with a deposition number of CGMCC No. 2568.

In the present disclosure, an EPS in the EPS solution of the microorganism preferably has a concentration of 2 to 16 g/L, more preferably 16 g/L; the ratio between a mass of the nanomaterial and a volume of the EPS solution of the microorganism is preferably from 2 to 20 g:1 L, more preferably 8 g/L.

The nanomaterial in the nanocomposite preparation provided by the present disclosure may, on the one hand, provide a carrier for the EPS and PAHs to come into contact with each other and enrich both PAHs and the EPS, thereby accelerating the interaction between the EPS and PAHs, and on the other hand, accelerate the electron transfer process during the degradation of PAHs by the EPS. In addition, the nanomaterial and EPS system may improve the bioeffectiveness of PAHs in soil compared with a single system, thus accelerating and improving the degradation of PAHs. The present disclosure makes full use of the high surface activity of the nanomaterial and the degradation properties of the EPS of the degrading bacteria, and the synergistic effect between the two significantly accelerates and enhances the degradation and removal of PAHs from soil and water, increasing the degradation and removal rate of PAHs, thus greatly reducing the remediation cycle of PAH-contaminated soil and water.

The present disclosure also provides a method for preparing the nanocomposite preparation described in the above technical solution, including the steps of:

- inoculating *P. aminovorans* HPD-2 in a culture medium and isolating a resulting culture system to obtain bacteria;
- washing and resuspending the bacteria to obtain a microbial solution;
- subjecting the microbial solution to sonication, centrifugation and filtration in turn to obtain the EPS solution of the microorganism; and
- dispersing the nanomaterial in the microbial EPS solution to obtain the nanocomposite preparation.

In the present disclosure, *P. aminovorans* HPD-2 is inoculated in a culture medium and a resulting culture system is isolated to obtain a culture solution.

In the present disclosure, the medium is preferably a liquid luria-bertani (LB) medium. There are no special limitations to the method of inoculation and culture in the present disclosure, and it is sufficient to use methods of inoculation and culture known in the art.

In an embodiment of the present disclosure, the liquid LB medium specifically includes: 5.0 g/L of yeast extract, 10.0 g/L of peptone, 10.0 g/L of NaCl, and a balance of deionized water, with a pH of 7.0, and the medium is sterilized at 0.12 MPa, 121° C. for 20 min for further use.

In the present disclosure, an inoculation rate of *P. aminovorans* HPD-2 into the medium is preferably 1%.

In an embodiment of the present disclosure, the incubation of the microorganisms is carried out as follows: a microbial solution of *P. aminovorans* HPD-2 stored at −80° C. is taken, 100 μL of the microbial solution of *P. aminovorans* HPD-2 is inoculated into 10 mL of liquid LB medium for re-culture at 30° C. and 150 r/min for 8 h, and the re-cultured solution is then inoculated into liquid LB medium at a volume ratio of 10% for a 16 h incubation.

After the solution is obtained, in the present disclosure, the culture medium is subjected to isolation and the bacteria are obtained.

In the present disclosure, the isolation is preferably achieved by centrifugation at preferably 5000-8000 rpm, more preferably 6000-7000 rpm, and preferably for 5-15 min, more preferably for 5-10 min.

After the bacteria are obtained, in the present disclosure, the bacteria are preferably subjected to washing and resuspension to obtain a microbial solution.

In the present disclosure, a reagent used for the washing and resuspension is independently preferably a phosphate buffer. In the present disclosure, the phosphate buffer preferably has a concentration of 0.2 mol/L and a pH of 7.4.

In the present disclosure, the washing is preferably repeated twice.

There is no special limitation to the resuspension in the present disclosure, and it is sufficient to conduct the resuspension by methods known in the art to make the microbial solution meet the requirements.

In the present disclosure, the OD600 value of the microbial solution is preferably 0.6 to 1.2, more preferably 0.8 to 1.0.

After the microbial solution is obtained, in the present disclosure, the microbial solution is subjected to sonication.

In the present disclosure, the sonication is preferably performed at room temperature for 10 min, with a sonication power of preferably 240 W.

After the sonication, in the present disclosure, the sonicated microbial solution is subjected to centrifugation.

In the present disclosure, the centrifugation is conducted at preferably 5000 to 8000 rpm, more preferably 5000 rpm, and preferably for 10 to 15 min, more preferably for 10 min.

After the centrifugation, in the present disclosure, a resulting supernatant of the microbial solution obtained by centrifugation is subjected to filtration to obtain the EPS solution of the microorganism.

In the present disclosure, the filtration is preferably carried out using a 0.22 m filter membrane.

After the EPS solution of the microorganism is obtained, in the present disclosure, the nanomaterial is dispersed in the EPS solution of the microorganism to obtain the nanocomposite preparation.

In the present disclosure, there is no particular limitation to the method of the dispersion, and it is sufficient to use a dispersion method well known in the art.

The nano-composite preparation provided by the present disclosure is simple to operate, cost-effective, promising for large-scale industrial production and suitable for in-situ remediation of PAH-contaminated soil and water without secondary contamination.

The present disclosure also provides use of the nanocomposite preparation described in the above technical solution or a nanocomposite preparation prepared by the method described in the above technical solution in the remediation of PAH-contaminated water and soil.

In the present disclosure, the nanocomposite preparation is preferably 2.5% by volume of the PAH-contaminated water.

In the present disclosure, the nanocomposite preparation is preferably 10% by dry weight of the PAH-contaminated soil.

In the present disclosure, the PAH species preferably includes one or more of phenanthrene, pyrene and benzo[a]pyrene, more preferably benzo[a]pyrene; the content of PAHs in the PAH-contaminated soil is preferably 1 to 50 mg/kg, more preferably 5 to 20 mg/kg; the content of PAHs in the PAH-contaminated water is preferably 1 to 50 mg/L, more preferably 5 to 20 mg/L.

In an embodiment of the present disclosure, the nanocomposite preparation in the remediation of PAH-contaminated soil is applied by specifically adding the nanocomposite preparation to the PAH-contaminated soil, mixing them well, adjusting the soil water content to 60% of the field water holding capacity and leaving it to incubate; the incubation is preferably performed at 30° C. for 15 d.

In an embodiment of the present disclosure, the nanocomposite preparation is applied in the remediation of PAH-contaminated water specifically by adding the nanocomposite preparation to the PAH-contaminated water and then incubating them for remediation. In the present disclosure, the incubation method is preferably oscillating incubation at 30° C. for more than 12 h, more preferably for 24 h.

The technical solutions in the present disclosure will be clearly and completely described below in connection with the examples in the present disclosure, but they are not to be understood as a limitation of the protection scope of the present disclosure.

Example 1

LB medium was prepared according to the following ingredients and amounts: yeast extract 5.0 g/L, peptone 10.0 g/L, NaCl 10.0 g/L, and a balance of deionized water, with the pH adjusted to 7.0. The medium was sterilized at 0.12 MPa, 121° C. for 20 min for further use. The microbial solution of *P. aminovorans* stored at −80° C. was taken and 100 L of the microbial solution of *P. aminovorans* HPD-2 was inoculated into 10 mL of liquid LB medium for re-culture at 30° C. and 150 rpm for 8 h, and then inoculated into liquid LB medium at 10% by volume for incubation for 16 h. After centrifugation at 6000 rpm for 5 min, the suspension was washed twice with phosphate buffer (0.2 mol/L, pH 7.4) and resuspended, and the OD600 value was adjusted to 1.0 to obtain *P. aminovorans* HPD-2. The supernatant was then centrifuged for 10 min at room temperature (power 240 W) and centrifuged at 5000 rpm for 10 min. The supernatant was filtered through a 0.22 m membrane, and the filtered liquid was used as an EPS solution, the concentration of which was 2 g/L. GO was uniformly dispersed in the EPS solution of *P. aminovorans* at a concentration of 2 g/L to obtain the nanocomposite preparation (EPS+GO).

Example 2

This example was the same with Example 1 except that GO was replaced with multi-walled CNT to obtain a nanocomposite preparation (EPS+CNT).

Example 3

LB medium was prepared according to the following ingredients and amounts: yeast extract 5.0 g/L, peptone 10.0 g/L, NaCl 10.0 g/L, and a balance of deionized water, with the pH adjusted to 7.0. The medium was sterilized at 0.12 MPa, 121° C. for 20 min for further use. The microbial solution of *P. aminovorans* stored at −80° C. was taken and 100 μL of the microbial solution of *P. aminovorans* HPD-2 was inoculated into 10 mL of liquid LB medium for re-culture at 30° C. and 150 rpm for 8 h, and then inoculated into liquid LB medium at 10% by volume for incubation for 16 h. After centrifugation at 5000 rpm for 10 min, logarithmic growth phase cells of the bacteria were obtained; the suspension was washed twice with phosphate buffer (0.2 mol/L, pH 7.4) and resuspended, and the OD600 value was adjusted to 1.0 to obtain *P. aminovorans* HPD-2. The supernatant was then centrifuged for 10 min at room temperature (power 240 W) and centrifuged at 5000 rpm for 10 min. The supernatant was filtered through a 0.22 μm membrane, and the filtered liquid was used as an EPS solution, the concentration of which was 2 g/L. GO was uniformly dispersed in the EPS solution of *P. aminovorans* at a concentration of 4 g/L to obtain the nanocomposite preparation (EPS+GO).

Example 4

This example was the same with Example 3 except that the GO was replaced with multi-walled CNT to obtain the nanocomposite preparation (EPS+CNT).

Example 5

This example was the same with Example 3 except that the concentration of the added GO was set to 0.004 g/L, 0.04 g/L, 0.4 g/L, 1 g/L, 2 g/L, 8 g/L, and 20 g/L, respectively.

Example 6

This example was the same with Example 3 except that the concentration of the EPS added for the preparation of the nanocomposite preparation was set to 0.5 g/L, 1 g/L, 4 g/L, 8 g/L, and 16 g/L, respectively.

Comparative Example 1

This example was the same with Example 1 except that only the EPS solution of *P. aminovorans* was used, and no nanomaterial was added.

Comparative Example 2

This example was the same with Example 1 except that only GO was added.

Comparative Example 3

This example was the same with Example 2 except that only multi-walled carbon nanotubes (CNT) were added.

Application Example 1

The BaP-contaminated soil was prepared using tidal soils collected from Fengqiu, with BaP as the representative PAHs, and the BaP content in the soil was 23 mg/kg. The nanocomposite preparation (EPS+GO) prepared in Example 1 was spiked into the soil at a ratio of 10% by dry soil weight, mixed and placed in an incubator for incubation at 30° C. for 15 d.

Application Example 2

This example was the same with Application Example 1 except that the nanocomposite preparation prepared in Example 1 was replaced by the nanocomposite preparation (EPS+CNT) prepared in Example 2.

Application Example 3

A solution of BaP at a concentration of 5 mg/L was used as the test water, the nanocomposite preparation (EPS+GO) prepared in Example 3 was added to the test water at a ratio of 2.5% (v/v), and the test water was incubated in a shaker at 30° C. and 150 r/min for 24 h.

Application Example 4

This example was the same with Application Example 3 except that the nanocomposite preparation prepared in Application Example 3 is replaced by the nanocomposite preparation (EPS+CNT) prepared in Example 4.

Application Example 5

This example was the same with Application Example 3 except that the nanocomposite preparation prepared in Application Example 3 was replaced by the nanocomposite preparation containing different concentrations of GO (EPS+GO) prepared in Example 5.

Application Example 6

This example was the same with Application Example 3 except that the nanocomposite preparation prepared in Example 3 was replaced with the nanocomposite preparation containing different concentrations of EPS (EPS+GO) prepared in Example 6.

Comparative Application Example 1

This example was the same with Application Example 1 except that the nanocomposite preparation prepared in Example 1 was replaced with the EPS solution of *P. aminovorans* prepared in Comparative Example 1.

Comparative Application Example 2

This example was the same with Application Example 1 except that the nanocomposite preparation prepared in Example 1 was replaced with the GO prepared in Comparative Example 2.

Comparative Application Example 3

This example was the same with Application Example 1 except that the nanocomposite preparation prepared in Example 1 was replaced with multi-walled CNT in Comparative Example 3.

Comparative Application Example 4

This example was the same with Application Example 1 except that the contaminated soil (CK) was used as a control and no remediation aid was added.

Comparative Application Example 5

A solution of BaP at a concentration of 5 mg/L was used as the test water, and the EPS solution of Comparative Example 4 was added to the test water at a rate of 2.5% (v/v) and the mixed solution was incubated in a shaker at 30° C. and 150 rpm for 24 h.

Performance Tests (1) The content of BaP in the soil after incubation in Application Examples 1 to 2 and Comparative Application Examples 1 to 4 was measured and the removal rate was calculated. The results are shown in FIG. 1.

As can be seen from FIG. 1, after 15 d of remediation, the nanocomposite preparation (EPS+GO) prepared in Example 1 showed a 68.37% removal rate of BaP from the soil, which was 59.72% higher compared to the control (CK) without any added remediation, significantly contributing to the removal of BaP from the soil. Compared to those in the treatment group added with GO only or microbial EPS only, the removal of BaP from the soil was also significantly improved by 39.42% and 42.53%, respectively.

As seen in FIG. 1, after 15 d of remediation, the nanocomposite preparation (EPS+CNT) prepared in Example 2 showed a 47.58% removal of BaP from the soil, with an increase of 38.93% compared to the control (CK) without any remediation, significantly contributing to the removal of BaP from the soil. Compared to those in the treatment group added with only multi-walled CNT or only microbial EPS, the removal of BaP from the soil was also significantly improved by 26.2% and 18.63%, respectively.

As can be seen in FIG. 1, after 15 d of remediation, the BaP removal rate in the control (CK) without any remediation was only 8.65%.

As can be seen from FIG. 1, after 15 d of remediation, the addition of microbial EPS alone resulted in 28.95% removal of BaP from the soil, which was a significant increase of 20.3% compared to the control (CK) without any remediation.

As can be seen from FIG. 1, after 15 d of remediation, the removal rate of BaP from the soil by the addition of GO alone was 25.84%, with a significant increase of 17.2% compared to the control treatment (CK) without the addition of any remediator.

As can be seen from FIG. 1, after 15 d of remediation, the removal rate of BaP from the soil by adding only multi-walled CNT was 21.38%, which was 12.73% higher than that of the control treatment (CK) without any remediator.

(2) The residual concentrations of BaP in the mixed aqueous solutions of Application Examples 3 to 4 and Comparative Application Example 5 were sampled at certain times and the removal rate of BaP in the aqueous solutions was calculated. The results are shown in FIG. 2.

Figure 2:
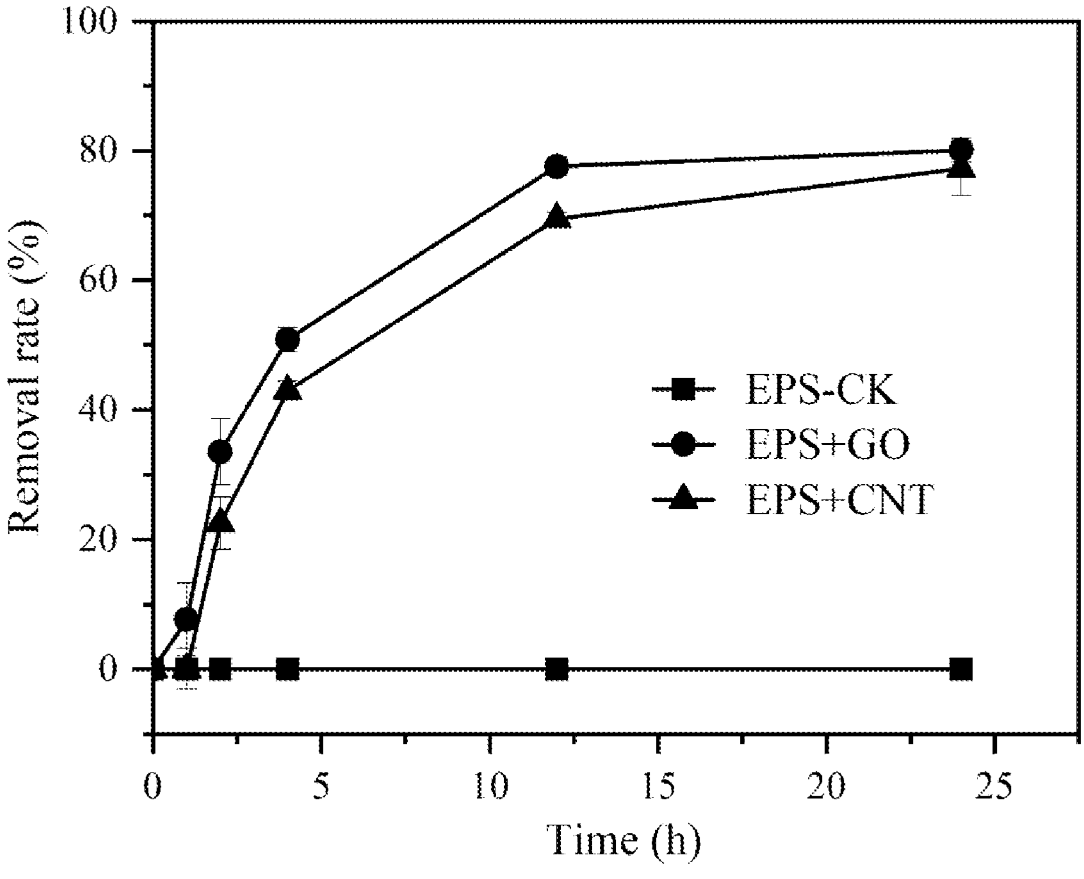
FIG. 2 shows a plot of the removal rate of BaP in mixed aqueous solutions from Application Examples 3 to 4 and Comparative Application Example 5 of the present disclosure.

As can be seen from FIG. 2, the nanocomposite preparation (EPS+GO) prepared in Example 3 achieved 77.6% removal of BaP from the aqueous solution after 12 h incubation, while the addition of EPS in Comparative Example 5 did not have any degradation effect on BaP in the aqueous solution. When the incubation time was extended to 24 h, the BaP removal rate of the nanocomposite preparation (EPS+GO) prepared in Example 3 slightly increased to 80.1% in the test water.

As can be seen in FIG. 2, after 12 h of incubation, the BaP removal from the test water by the nanocomposite preparation (EPS+CNT) prepared in Example 4 reached 69.5%, whereas the addition of EPS only in Example 5 had no effect on BaP degradation in the solution. When the incubation time was extended to 24 h, the rate of BaP degradation and removal in the test water by the nanocomposite preparation (EPS+CNT) prepared in Example 4 continued to increase, reaching 77.2%.

As seen in FIG. 2, the addition of EPS only did not degrade BaP in the solution during the 24 h incubation.

(3) The residual concentrations of BaP in the mixed aqueous solutions added with the nanocomposite preparations containing different concentrations of GO in Example 5 were sampled separately and the removal rate of BaP from the aqueous solutions was calculated. The results are shown in FIG. 3.

Figure 3:
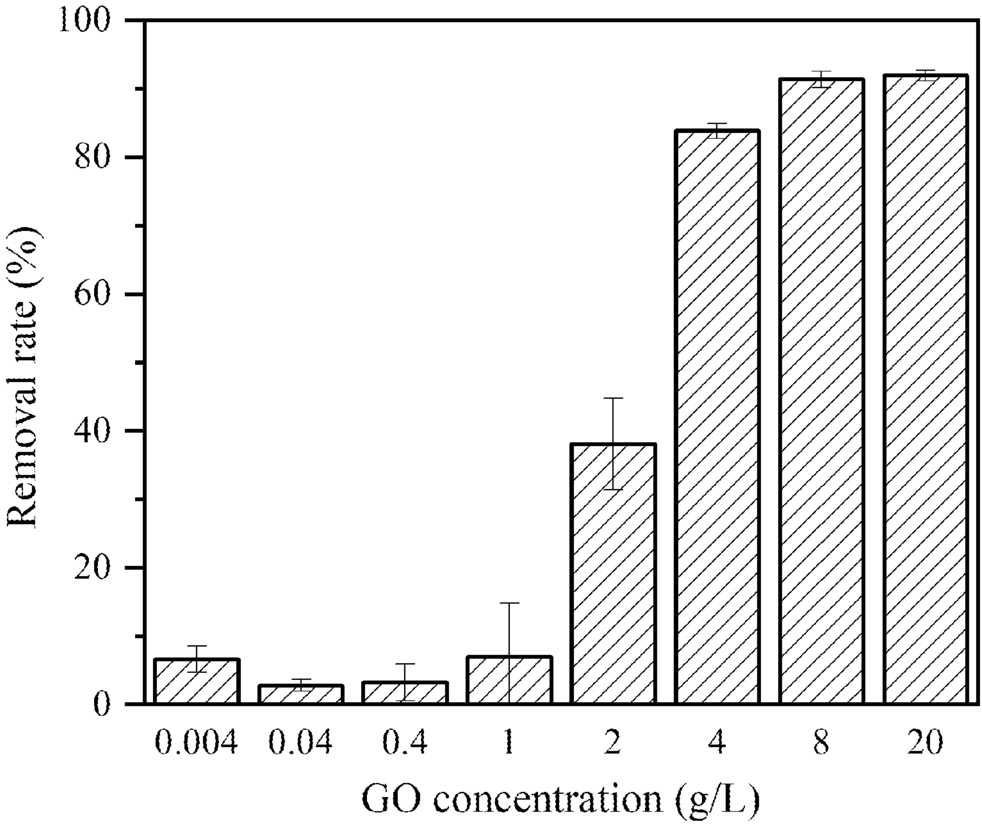
FIG. 3 shows a histogram of the removal rate of BaP in mixed aqueous solutions containing nanocomposite preparations with different concentrations of GO in Application Example 5 of the present disclosure.

As can be seen from FIG. 3, the degradation effect of the nanocomposite preparation prepared from GO and EPS solution on BaP in aqueous solution was more limited when the GO addition was 0.004-1 g/L after 24 h incubation, which was only 2.8-6.9%. When GO was added at 2 g/L, the degradation rate of BaP in water was 38.1% for the nanocomposite preparation prepared from GO and EPS solution. The degradation rate of BaP in water was significantly increased with the increasing addition of GO, and the degradation rate of BaP in water by the nanocomposite preparation prepared from GO and EPS solution reached 83.9-92.0% when the addition of GO was 4-20 g/L.

(4) The residual concentrations of BaP in the mixed aqueous solutions added with the nanocomposite preparation containing different concentrations of *P. aminovorans* EPS solutions in Application Example 6 were sampled separately and the removal rates of BaP in the aqueous solutions were calculated. The results are shown in FIG. 4.

Figure 4:
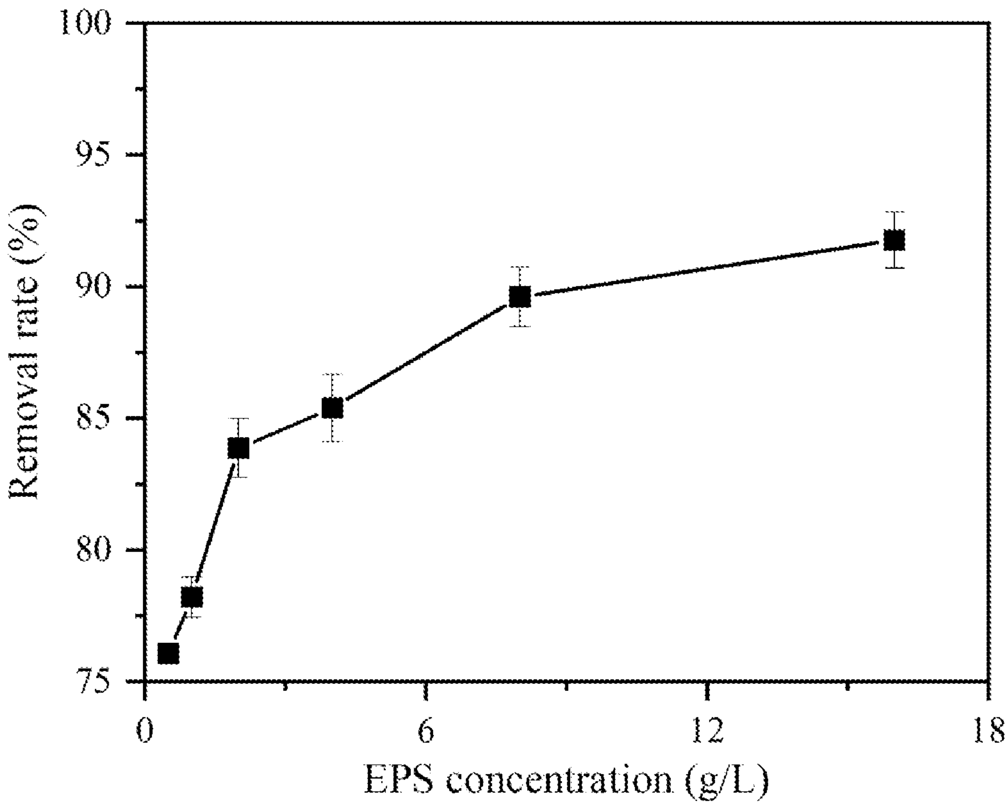
FIG. 4 shows a plot of the removal rate of BaP in the mixed aqueous solution containing nanocomposite preparations with different concentrations of EPS solutions of *P. aminovorans* in Application Example 6 of the present disclosure.

As can be seen from FIG. 4, the removal rate of BaP from the aqueous solution by the nanocomposite preparation prepared from GO and EPS solution increased continuously as the addition amount of EPS increased, and the removal rate of BaP in the aqueous solution by this nanocomposite preparation was 76.3% and 78.1% when the addition amount of EPS was 0.5 g/L and 1 g/L, respectively. As the addition of EPS increased to more than 2 g/L, the removal rate of BaP in the water body reached more than 85%, and when the addition of EPS was 16 g/L, the removal rate of BaP in the water body of this compound system could reach 92%.

Although the above examples provide an exhaustive description of the disclosure, it is only a part of the embodiments of the disclosure and not all of them, and one can obtain other embodiments according to the present embodiments without an inventive step, all of which are within the protection scope of the disclosure.

What is claimed is:

1. A nanocomposite preparation, comprising a nanomaterial and an extracellular polymeric substance (EPS) solution of a microorganism, wherein the nanomaterial is graphene oxide (GO) or multi-walled carbon nanotubes (CNT); and the microorganism is *Paracoccus aminovorans* (*P. aminovorans*) HPD-2, deposited in China General Microbiological Culture Collection (CGMCC) Center, with a deposition number of CGMCC No. 2568; the EPS solution is cell-free, and the EPS in the EPS solution has a concentration of 2 to 16 g/L.

2. The nanocomposite preparation of claim 1, wherein a ratio between a mass of the nanomaterial and a volume of the EPS solution of the microorganism is 2 to 20 g:1 L.

3. A method for preparing the nanocomposite preparation of claim 1, comprising inoculating *P. aminovorans* HPD-2 in a culture medium and isolating a resulting culture system to obtain bacteria;

washing and resuspending the bacteria to obtain a microbial solution;

subjecting the microbial solution to sonication, centrifugation and filtration in turn to obtain the EPS solution of the microorganism; and dispersing the nanomaterial in the EPS solution of the microorganism to obtain the nanocomposite preparation.

4. The method of claim 3, wherein the microbial solution has an OD600 value of 0.6 to 1.2.

5. The method of claim 3, wherein the filtration is carried out with a 0.22 μm filter membrane.

6. The method of claim 3, wherein the sonication is carried out at room temperature; and the sonication lasts for 10 min with a sonication power of 240 W.

7. The method of claim 3, wherein a ratio between a mass of the nanomaterial and a volume of the EPS solution of the microorganism is 2 to 20 g:1 L.

8. A method for remediating PAH-contaminated water, comprising administering the nanocomposite preparation of claim 1 to PAH-contaminated water.

9. The method of claim 8, wherein the nanocomposite preparation is 2.5% by volume of the PAH-contaminated water body.

10. The method of claim 8, wherein the nanocomposite preparation is 10% by dry weight of the PAH-contaminated soil.

11. The method of claim 8, wherein a ratio between a mass of the nanomaterial and a volume of the EPS solution of the microorganism is 2 to 20 g:1 L.

* * * * *